US007186852B1

(12) United States Patent
Rogers et al.

(10) Patent No.: US 7,186,852 B1
(45) Date of Patent: Mar. 6, 2007

(54) SHEA BUTTER DIMETHYL AMIDOPROPYL AMINES

(75) Inventors: Steven Rogers, Yardley, PA (US); Anthony O'Lenick, Jr., Dacula, GA (US)

(73) Assignee: Rutherford Chemicals, LLC, Bayonne, NJ (US)

( * ) Notice: Subject to any disclaimer, the term of this patent is extended or adjusted under 35 U.S.C. 154(b) by 0 days.

(21) Appl. No.: 11/347,269

(22) Filed: Feb. 6, 2006

(51) Int. Cl.
*C07C 231/00* (2006.01)
(52) U.S. Cl. .......................................... 554/51; 554/69
(58) Field of Classification Search ................. 554/51, 554/69
See application file for complete search history.

(56) References Cited

U.S. PATENT DOCUMENTS 5,741,915 A * 4/1998 O'Lenick, Jr. ............... 554/52
6,552,208 B1 * 4/2003 Alander et al. ............. 554/208

* cited by examiner

*Primary Examiner*—Deborah D. Carr
(74) *Attorney, Agent, or Firm*—Louis C. Paul

(57) ABSTRACT

Novel dimethyl amidopropyl amines prepared by the reaction of dimethyl amidopropyl amine (DMAPA) and shea butter, preferably mild-processed shea butter (MPSB). Materials of the present invention are useful as cosmetic and personal care ingredients, allowing for the delivery of highly desirable active ingredients present in shea butter including natural antioxidants, in a cationic material that is substantive to the skin and hair.

7 Claims, No Drawings

SHEA BUTTER DIMETHYL AMIDOPROPYL AMINES

CROSS-REFERENCE TO RELATED APPLICATIONS

Not applicable.

STATEMENT REGARDING FEDERALLY-SPONSORED RESEARCH OR DEVELOPMENT

Not applicable.

FIELD OF THE INVENTION

The present invention relates to novel shea butter dimethyl-amidopropyl amines, prepared by the reaction of dimethyl amidopropyl amine (DMAPA) and shea butter, preferably mild-processed shea butter (MPSB). These compounds are useful as cosmetic and personal care ingredients, allowing for the delivery of highly desirable active ingredients present in shea butter, including natural antioxidants, in a cationic material that is substantive to the skin and hair.

BACKGROUND OF THE INVENTION

Amidoamines are well-known raw materials used as conditioning agents in the cosmetic and personal care products and conform to the following structure:

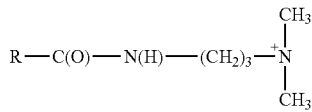

At the extremes of the pH range, amidoamines are non-protonated.

Shea butter is a butter extracted from the kernel of *Butrospermum parkii*. This plant, also referred to as *Vitellaria paradoxa*, is native to Africa. The term butter describes a material that is a solid at room temperature, but melts at about 40° C. Chemically, shea butter is a triglyceride conforming to the following structure:

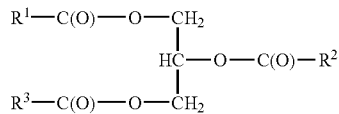

wherein $R^1$, $R^2$ and $R^3$ each have one of the following compositions:

| R Group | Common Name | Range (%) | Typical (%) |
|---|---|---|---|
| $C_{11}H_{23}$ | Lauryl | 0.1–2.0 | 0.2 |
| $C_{13}H_{27}$ | Myristyl | 0.5–2.0 | 1.0 |
| $C_{15}H_{31}$ | Cetyl | 2.0–6.0 | 4.0 |
| $C_{17}H_{35}$ | Stearyl | 25.0–50.0 | 35.0 |
| $C_{17}H_{33}$ | Oleyl | 40.0–60.0 | 59.0 |
| $C_{17}H_{31}$ | Linoleyl | 0.5–1.0 | 0.8 |

The average composition of $R^2$ is different than $R^1$ and $R^3$, the latter two being similar. The $R^2$ moiety contains predominantly the unsaturated $C_{18}$ group (oleyl) while $R^1$ and $R^3$ contain predominantly the saturated $C_{18}$ group (stearyl). Differences between internal ($R^2$) and terminal ($R^1$, $R^3$) substitution are seen in natural products but not in synthetic molecules produced in the laboratory.

The high levels of stearyl and oleyl groups make shea butter and its DMAPA derivatives of particular interest in the personal care industry. While other raw materials used in personal care products have these species, the compounds of the present invention have significantly high concentrations of unsaponifiables, which posses highly desired antioxidant, ultra-violet radiation protection, and free-radical scavenging properties. Mild-processed shea butter typically contains from about 5% to about 15% by weight of unsaponifiables. In contrast, other butters commonly used in personal care products have less than 2% unsaponifiables. For example, coca butter (from *Theobroma cacao*) averages 0.4% unsaponifiables and Illipe butter (from *Shorea stenoptera*) averages 1.1%.

As described in greater detail below, the novel shea butter DMAPA compounds of the present invention are produced by reacting shea butter, preferably MPSB, with DMAPA, preferably under specific mild processing conditions. By "mild processed" is meant processes that do not remove or otherwise diminish the amount or potency of active ingredients, particularly highly desired unsaponifiables, from the mild-processed shea butter. In one aspect of the present invention, mild processing is employed both at the time of harvesting and initial extraction and during subsequent preparation of derivatives. These mild processes result in materials containing unexpectedly high amounts unsaponifiables, notably antioxidants.

U.S. Pat. No. 5,741,915 discloses betaine compounds based on meadowfoam, including the use of meadowfoam amidopropyl dialkyl amine intermediate in the preparation of meadowfoam-based betaines. While providing conditioning properties, the materials described in the '915 patent do not possess the desirable unsaponifiable fractions, and with them antioxidant properties, of the compounds of the present invention.

The shea butter DMAPA derivatives of the present invention thus deliver unexpectedly high amounts of unsaponifiables containing antioxidants to the skin and hair in a heretofore unachievable manner.

SUMMARY OF THE INVENTION

The compounds of the present invention are shea butter dimethyl amidopropyl amines produced by reacting shea butter with dimethyl amidopropyl amine under mild conditions. In a preferred aspect of the present invention, mild processing is employed both at the time of harvesting and initial extraction (creating mild-processed shea butter) and during subsequent preparation of DMAPA derivatives. The novel DMAPA compounds of the present invention are rich in unsaponifiables, including antioxidants.

DETAILED DESCRIPTION OF THE INVENTION

The compounds of the present invention are novel amidoamines, specifically dimethyl aminopropyl amines (DMAPA), produced by reacting shea butter with DMAPA. Preferably the shea butter is mild-processed and is reacted with DMAPA under mild processing conditions. The novel DMAPA compounds of the present invention are rich in unsaponifiables, including antioxidants and free-radical scavengers.

Shea butter dimethyl amidopropyl amine derivatives of the present invention conform to the following structure:

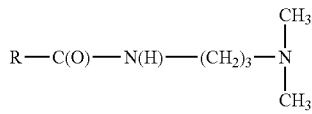

wherein
R is derived from shea butter and comprises
from about 0.1 to about 2.0% by weight $C_{11}H_{23}$;
from about 0.5 to about 2.0% by weight $C_{13}H_{27}$;
from about 2.0 to about 6.0% by weight $C_{15}H_{31}$;
from about 25 to about 50% by weight $C_{17}H_{35}$; and
from about 40.0 to about 60.0% by weight $C_{17}H_{33}$.

Another aspect of the present invention is a process for delivering antioxidants to the skin or hair by topically applying a finished product comprising an effective amount of the above-described shea butter DMAPA derivative. In a preferred embodiment, the effective concentration ranges from about 0.1% to about 15.0% by weight of the total finished product.

Shea Butter

Shea butter can be prepared by standard extraction techniques known to those of skill in the art. For example, U.S. Pat. No. 6,552,208, the disclosure of which is incorporated herein by reference, describes several methods for processing shea butter. Suitable extraction vehicles may include, but are not limited to, ethanol, methanol, ethyl acetate, acetone, chloroform and water, or any other solvent and water.

In a preferred aspect of the present invention, shea butter is mild-processed; it is extracted using a hydrocarbon-free solvent system and its DMAPA derivatives are made under mild processing conditions. At the time of harvesting and initial extraction ground-up kernels are boiled in water under mild conditions as described in the examples below. The oil phase is then separated from the water phase by decanting. This process yields a yellow, solid wax rich in unsaponifiables. By wax is meant a material obtained by boiling in water under ambient conditions, decanted and filtered.

The mild processing conditions of the present invention may be contrasted with separation using solvents and high temperature treatment with high pressure steam. While the latter processes result in what some may describe as a "more pure" triglyceride, unsaponifiables, and the benefits derived therefrom, are lost. Vacuum distillation which strips off the desirable components is also to be avoided in processing MPSB of the present invention. By processing shea butter under mild conditions, materials comprising from about 5% to about 15% by weight of unsaponifiables can be produced.

Sterols comprise about 20% of the unsaponifiables in shea butter. More particularly, the sterols comprise: cholesterol (from about 1% to about 3%); alpha-spinasterol (from about 1% to about 4%); delta-7-stigmasterol (from about 40% to about 44%); delta-7-avenasterol (from about 38% to about 41%). The remaining constituents of the unsaponifiables (about 80%) include other highly desirable active compounds including tocopherol, karitin, cinamic acid esters, alpha and beta amyrin and phenolics.

Phenolic compounds are natural products composed of one or more aromatic benzene rings with one or more hydroxyl group. They are a class of natural products that possess antioxidant and free radical scavenging properties. Among the phenolics in the unsaponifiables of mild-processed shea butter include gallic acid, gallocatchin, catechin, epigallocatechin gallate, epicatechin, gallocatechin gallate, gallocatechin gallate and quercetin.

Dimethyl amidopropyl amine

Dimethyl amidopropyl amine is an item of commerce with a molecular formula of $C_5H_{14}N_2$ and the following structural formula:

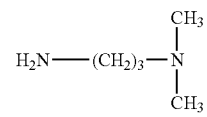

It is commercially available from a number of raw materials suppliers, including BASF (Mount Olive, N.J.).

Another aspect of the present invention is a shea butter DMAPA made by the amidation reaction of dimethyl aminopropyl amine and shea butter, preferably mild-processed. In a preferred embodiment, the amidation is conducted at a temperature of from about 180° C. to about 190° C.

The following examples are further illustrative of the present invention. The components and specific ingredients are presented as being typical, and various modifications can be derived in view of the foregoing disclosure within the scope of the invention. All percentages, ratios and proportions herein are by weight, unless otherwise specified. All temperatures are in degrees Celsius unless otherwise specified.

EXAMPLES

The starting MPSB is made according to following procedure: 500.0 grams of the nut form the shea butter tree are cracked into small pieces and placed into a one-liter vat of water. The water is then heated to 100° C. As the temperature increases, an oil phase develops on the surface of the water. The temperature is held for about 2 hours, after which the oil is decanted and passed through filter paper. The resulting butter is mild-processed shea butter according to the present invention. It is rich in unsaponifiable (from about 7% to about 15% by weight) and may be used in making the mild-processed shea butter DMAPA derivatives of the present invention.

To 455.0 grams of DMAPA is added 1450.0 grams of MPSB. Using a reflux condenser, the temperature of the mass is raised to 180° C.–190° C. The mass is held within this temperature range for 8–10 hours. The amine value drops during this period and, after several hours, stabilizes. Once the amine value stabilizes, the reaction mass is held an additional hour and is cooled to ambient temperature. Essential to the preparation of mild-processed shea butter DMAPA compounds of the present invention is the low processing temperatures. This requires neither distillation of water or processing at high temperatures (e.g., from about 180° C. to about 190° C.).

The mild-processed shea butter DMAPA derivatives of the present invention can be added to shampoos and body wash formulations in which the pH is then adjusted to neutral with acid including, but not limited to, hydrochloric acid, citric acid, glycolic acid, phosphoric acid, and salicylic acid.

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth hereinabove but rather that the claims be construed as encompassing all the features of patentable novelty which reside in the present invention, including all features which would be treated as equivalents thereof by those skilled in the art to which the invention pertains.

The invention claimed is:

1. A shea butter dimethyl aminopropyl amine conforming to the structure:

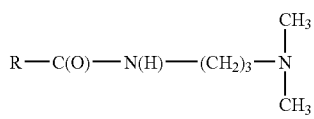

wherein

R is derived from shea butter and comprises
from about 0.1 to about 2.0% by weight $C_{11}H_{23}$;
from about 0.5 to about 2.0% by weight $C_{13}H_{27}$;
from about 2.0 to about 6.0% by weight $C_{15}H_{31}$;
from about 25 to about 50% by weight $C_{17}H_{35}$; and
from about 40.0 to about 60.0% by weight $C_{17}H_{33}$.

2. A DMAPA derivative of claim 1 made by the amidation reaction of dimethyl amidopropyl amine and mild-processed shea butter.

3. A DMAPA derivative of claim 2 wherein the amidation is conducted at a temperature of from about 180° C. to about 190° C.

4. A process for treating hair and skin with an effective concentration of a dimethyl amidopropyl amine made by the amidation reaction of dimethyl amidopropyl amine and shea butter.

5. A process for treating hair and skin of claim 4 wherein the amidation is conducted at a temperature of from about 180° C. to about 190° C.

6. A shea butter dimethyl aminopropyl amine of claim 1 where the shea butter is mild-processed.

7. A process of claim 4 where the shea butter is mild-processed.

* * * * *